US00PP27849P3

(12) United States Plant Patent
Kobayashi

(10) Patent No.: US PP27,849 P3
(45) Date of Patent: Apr. 4, 2017

(54) POINSETTIA PLANT NAMED 'PER508'

(50) Latin Name: ***Euphorbia pulcherrima* Willd.**
Varietal Denomination: PER508

(71) Applicant: Ruth Kobayashi, Carlsbad, CA (US)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 107 days.

(21) Appl. No.: 14/545,488

(22) Filed: May 12, 2015

(65) Prior Publication Data

US 2016/0353640 P1 Dec. 1, 2016

(51) Int. Cl.
*A01H 5/02* (2006.01)

(52) U.S. Cl.
USPC ..... Plt./303

(58) Field of Classification Search
USPC ..... Plt./263.1, 302, 303
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of Poinsettia plant named 'PER508', characterized by its compact, uniform, upright and mounded plant habit; moderately vigorous growth habit; freely and upright branching habit; very dark green-colored leaves with sinuate margins that give the leaves a textured appearance; under natural season conditions, plants flower on or about December 5 in Southern California; large inflorescences with burgundy-colored flower bracts; and good post-production longevity.

1 Drawing Sheet

Botanical designation: *Euphorbia pulcherrima* Willd.
Cultivar denomination: 'PER508'.

BACKGROUND OF THE INVENTION

The present invention relates to a new and distinct cultivar of Poinsettia plant, botanically known as *Euphorbia pulcherrima* Willd., and hereinafter referred to by the cultivar name 'PER508'.

The new Poinsettia plant is a product of a planned breeding program conducted by the Inventor in Encinitas, Calif. The objective of the breeding program is to create new uniform Poinsettia plants having large inflorescences with attractive flower bracts and excellent post-production longevity.

The new Poinsettia plant is a naturally-occurring whole plant mutation of a proprietary selection of *Euphorbia pulcherrima* Willd. 'Eckadire', disclosed in U.S. Plant Pat. No. 12,846. The new Poinsettia plant was discovered and selected by the Inventor from within a population of plants of the mutation parent in a controlled greenhouse environment in Encinitas, Calif. on Sep. 14, 2007.

Asexual reproduction of the new Poinsettia plant by terminal vegetative cuttings in a controlled greenhouse environment in Encinitas, Calif. since January, 2008 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'PER508'. These characteristics in combination distinguish 'PER508' as a new and distinct Poinsettia plant:

1. Compact, uniform, upright and mounded plant habit.
2. Moderately vigorous growth habit.
3. Freely and upright branching habit.
4. Very dark green-colored leaves with sinuate margins that give the leaves a textured appearance.
5. Under natural season conditions, plants flower on or about December 5 in Southern California.
6. Large inflorescences with burgundy-colored flower bracts.
7. Good post-production longevity.

In side-by-side comparisons conducted in Encinitas, Calif., plants of the new Poinsettia differ primarily from plants of the mutation parent, 'Eckadire' in the following characteristics:

1. Plants of the new Poinsettia are more compact and less vigorous than plants of 'Eckadire'.
2. Plants of the new Poinsettia and 'Eckadire' differ in leaf texture as plants of 'Eckadire' have smooth, not textured, leaves.
3. Plants of the new Poinsettia and 'Eckadire' differ in flower bract color as plants of 'Eckadire' have dark red-colored flower bracts.
4. Plants of the new Poinsettia flower about five days later than plants of 'Eckadire' when grown under natural season conditions.

Plants of the new Poinsettia can be compared to plants of the *Euphorbia pulcherrima* Willd. '490', disclosed in U.S. Plant Pat. No. 7,825. In side-by-side comparisons conducted in Encinitas, Calif., plants of the new Poinsettia differed primarily from plants of '490' in the following characteristics:

1. Plants of the new Poinsettia were more compact and less vigorous than plants of '490'.
2. Plants of the new Poinsettia had a more upright branching habit than plants of '490'.
3. Plants of the new Poinsettia and '490' differed in flower bract color as plants of '490' had dark red-colored flower bracts.
4. Plants of the new Poinsettia flowered about 17 days later than plants of '490' when grown under natural season conditions.

Plants of the new Poinsettia can be compared to plants of the *Euphorbia pulcherrima* Willd. 'Eckanezka', disclosed in U.S. Plant Pat. No. 19,192. In side-by-side comparisons conducted in Encinitas, Calif., plants of the new Poinsettia differed primarily from plants of 'Eckanezka' in the following characteristics:

1. Plants of the new Poinsettia and 'Eckanezka' differed in leaf texture as plants of 'Eckanezka' had smooth, not textured, leaves.
2. Plants of the new Poinsettia and 'Eckanezka' differed in flower bract color as plants of 'Eckanezka' had dark red-colored flower bracts.
3. Plants of the new Poinsettia flowered about 15 days later than plants of 'Eckanezka'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph at the bottom of the sheet is a side perspective view of a typical flowering plant of 'PER508' grown in a container.

The photograph at the top of the sheet is a close-up view of a typical flowering plant of 'PER508'.

DETAILED BOTANICAL DESCRIPTION

Plants used in the aforementioned photographs and in the following detailed description were grown during the late autumn/early winter in 16.5-cm containers in a polyethylene-covered greenhouse in Encinitas, Calif. and under natural season conditions and cultural practices typical of commercial Poinsettia production. During the production of the plants, day temperatures averaged 25° C., night temperatures averaged 20° C. and light levels averaged 5,000 foot-candles. Measurements and numerical values represent averages for typical flowering plants. Plants were pinched one time and were 20 weeks old when the photographs and the description were taken. In the following description, color references are made to The Royal Horticultural Society Colour Chart, 2007 Edition, except where general terms of ordinary dictionary significance are used.

Botanical classification: *Euphorbia pulcherrima* Willd. 'PER508'.

Parentage: Naturally-occurring whole plant mutation of *Euphorbia pulcherrima* Willd. 'Eckadire', disclosed in U.S. Plant Pat. No. 12,846.

Propagation:

*Type*.—Terminal vegetative cuttings.

*Time to initiate roots*.—About seven to ten days at night temperatures about 20° C. and day temperatures about 27° C.

*Time to produce a rooted young plant*.—About four weeks at night temperatures about 20° C. and day temperatures about 27° C.

*Root description*.—Fibrous; white in color.

Plant description:

*Plant habit and form*.—Compact, uniform, upright and mounded plant habit; inverted triangle; large inflorescences positioned above the foliar plane; moderately vigorous growth habit.

*Plant height*.—About 36 cm.

*Plant diameter or spread*.—About 50 cm.

*Lateral branch description*.—Quantity: Freely branching habit, about nine lateral branches develop after pinching; upright branching habit. Length: About 30 cm. Diameter: About 7 mm. Internode length: About 2.6 cm. Strength: Strong. Aspect: Initially upright to somewhat outwardly. Texture: Smooth, glabrous. Luster: Glossy. Color: Close to 146A.

*Leaf description*.—Arrangement: Alternate, simple. Length: About 13.6 cm. Width: About 8.2 cm. Shape: Broadly lanceolate to elliptic with irregular rounded shallow lobes; margins sinuate giving the leaves a textured appearance. Apex: Acuminate. Base: Attenuate. Margin: Mostly entire with irregular shallow rounded lobes; sinuate. Aspect: Flat, textured. Venation pattern: Pinnate, arcuate. Texture, upper surface: Scattered pubescence. Texture, lower surface: Slightly pubescent; prominent venation. Color: Developing and fully expanded leaves, upper surface: Much darker green than 139A (approaching black); venation, close to N137A. Developing and fully expanded leaves, lower surface: Close to N137A; venation, close to midvein, close to 147C. Petioles: Length: About 10.6 cm. Diameter: About 2.5 mm. Texture, upper and lower surfaces: Smooth, glabrous. Luster, upper and lower surfaces: Glossy. Color, upper surface: Close to 187A. Color, lower surface: Close to 199A.

Inflorescence description:

*Inflorescence type and habit*.—Terminal inflorescences are compound corymbs of cyathia with colored flower bracts subtending the cyathia; inflorescences uniformly positioned above the foliar plane.

*Fragrance*.—None detected.

*Flowering response*.—Under natural season conditions, plants typically flower on or about December 5 in Southern California; under artificial long nyctoperiod/short photoperiod conditions, plants flower about eight to nine weeks later.

*Post-production longevity*.—Good post-production longevity; plants of the new Poinsettia maintain good substance and flower bract color for about four to six weeks under interior conditions; flower bracts persistent and cyathia not persistent.

*Inflorescence diameter*.—About 34 cm.

*Inflorescence height* (*depth*).—About 9.5 cm to 10 cm.

*Flower bracts*.—Quantity per inflorescence: About 18. Length, largest bracts: About 14.5 cm. Width, largest bracts: About 11.6 cm. Shape: Broadly lanceolate to elliptical with irregular rounded shallow lobes. Apex: Acuminate. Base: Attenuate. Margin: Mostly entire with irregular shallow rounded lobes; slightly sinuate. Texture, upper and lower surfaces: Smooth, glabrous; satiny; slightly rugose. Aspect: Upright to horizontal and with development, drooping. Venation pattern: Pinnate, arcuate. Color: Developing or transitional bracts, upper surface: Close to 187C. Developing or transitional bracts, lower surface: Close to 184B. Fully expanded bracts, upper surface: Close to 187B; color does not fade with development. Fully expanded bracts, lower surface: Close to 187D; color does not fade with development. Bract petioles: Length: About 5.5 cm. Diameter: About 2 mm. Texture, upper and lower surfaces: Smooth, glabrous. Color, upper and lower surfaces: Close to 187B.

*Cyathia*.—Quantity per corymb: About 13. Length: About 1.2 cm. Width: About 5 mm. Shape: Oval. Texture: Smooth, glabrous. Color, inner and outer surfaces: Close to 146A.

*Nectaries*.—Quantity per cyathium: One, occasionally two. Length: About 4 mm. Width: About 2.5 mm. Shape: Roughly elliptical to oval. Texture: Smooth, glabrous. Color, inner and outer surfaces: Close to 169B.

*Peduncles*.—Length: About 4 mm. Diameter: About 2 mm. Strength: Strong. Aspect: Mostly upright. Texture: Smooth, glabrous. Color: Close to 146B.

*Reproductive organs*.—Stamens: Quantity per cyathium: About ten to twelve. Filament length: About 3 mm. Filament color: Close to 187C. Anther shape: Round; bi-lobed. Anther length: About 1 mm. Anther color: Close to 160A. Amount of pollen: Scarce. Pollen color: Close to 14B. Pistils: Pistil development has not been observed on plants of the new Poinsettia.

*Seeds and fruits*.—Seed and fruit production have not been observed on plants of the new Poinsettia.

Disease & pest resistance: Plants of the new Poinsettia have not been shown to be resistant to pathogens and pests common to Poinsettia plants.

Temperature tolerance: Plants of the new Poinsettia have been observed to tolerate temperatures ranging from about 16° C. to about 29° C.

It is claimed:

1. A new and distinct Poinsettia plant named 'PER508' as illustrated and described.

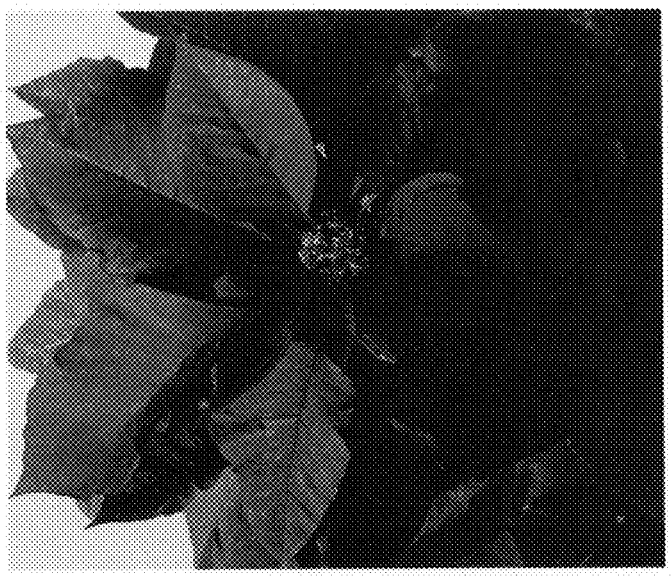
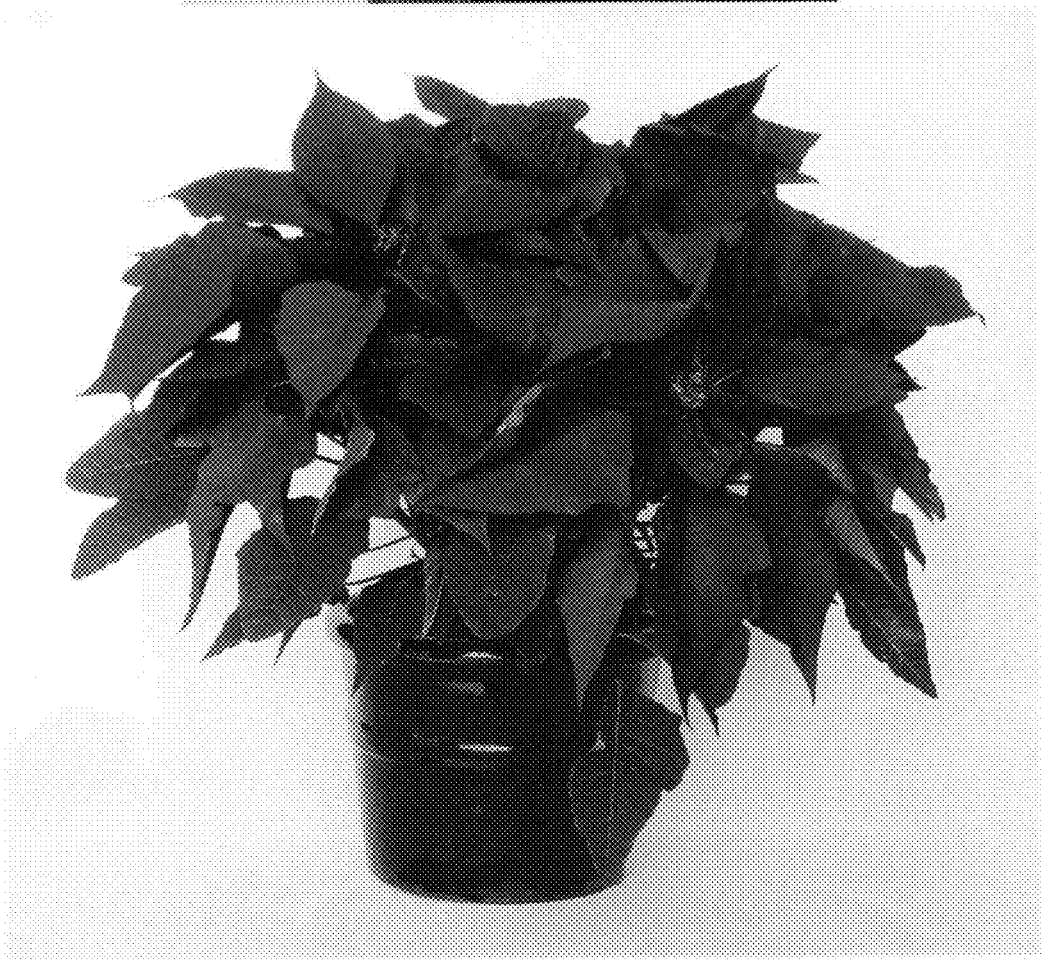

* * * * *